(12) United States Patent
Marcotte et al.

(10) Patent No.: US 11,469,061 B2
(45) Date of Patent: Oct. 11, 2022

(54) CONTROL DEVICE SENSOR ROTATION

(71) Applicant: GE Precision Healthcare LLC, Milwaukee, WI (US)

(72) Inventors: Julien Marcotte, Saint-Vrain (FR); Stephane Vandroux, Paris (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 44 days.

(21) Appl. No.: 16/802,441

(22) Filed: Feb. 26, 2020

(65) Prior Publication Data

US 2021/0265120 A1 Aug. 26, 2021

(51) Int. Cl.
| | |
|---|---|
| H01H 19/14 | (2006.01) |
| G05G 1/015 | (2008.04) |
| G05G 1/10 | (2006.01) |
| G05G 5/05 | (2006.01) |
| H01H 19/08 | (2006.01) |

(52) U.S. Cl.
CPC ............. *H01H 19/14* (2013.01); *G05G 1/015* (2013.01); *G05G 1/10* (2013.01); *G05G 5/05* (2013.01); *H01H 19/08* (2013.01); *H01H 2221/044* (2013.01)

(58) Field of Classification Search
CPC ...... H01H 19/14; H01H 19/11; H01H 19/585; H01H 19/58; H01H 19/62; H01H 19/635; H01H 19/64; H01H 19/63; H01H 19/005; H01H 19/10; H01H 1/2041; H01H 19/56; H01H 19/03; H01H 19/02;
(Continued)

(56) References Cited

U.S. PATENT DOCUMENTS 4,652,947 A * 3/1987 Oka ..................... G11B 15/026
200/11 R
6,307,304 B1 * 10/2001 Yorio ................... H01H 19/005
310/339

(Continued)

FOREIGN PATENT DOCUMENTS

| GB | 2533923 A | 7/2016 |
| JP | 2015005394 A | 1/2015 |

(Continued)

OTHER PUBLICATIONS

EP application 21156150.1 filed 09FEB2021—Extended Search Report dated Jul. 28, 2021; 7 pages.
(Continued)

*Primary Examiner* — Ahmed M Saeed
(74) *Attorney, Agent, or Firm* — McCoy Russell LLP

(57) ABSTRACT

A control device which allows an operator/user to follow the user's anatomical movement by following natural hand rotation, includes two independent detection sensors or sensor portions embedded in two different parts of the device, one in a fixed part and one in a mobile or rotative part, with resistance to mutual disturbance between the two. The device includes a knob portion rotatable about an axis of rotation, at least one sensor configured to sense a rotational position of the knob in relation to the axis of rotation, circuitry adapted to at least provide electrical power to the rotative knob portion, circuitry adapted to transmit the sensed rotational position of the knob, and a base portion rotatably coupled to the knob portion.

17 Claims, 4 Drawing Sheets

(58) Field of Classification Search
CPC .. H01H 2019/006; H01H 19/00; H01H 19/20; H01H 19/001; H01H 21/50; H01H 2221/01
See application file for complete search history.

(56) References Cited

U.S. PATENT DOCUMENTS

| | | |
|---|---|---|
| 10,027,323 B2 | 7/2018 | Tachiiri |
| 2006/0012584 A1 | 1/2006 | Vassallo |
| 2016/0183903 A1 | 6/2016 | Vandroux et al. |

FOREIGN PATENT DOCUMENTS

| | | |
|---|---|---|
| WO | 2012075468 A1 | 6/2012 |
| WO | 2014020376 A1 | 2/2014 |

OTHER PUBLICATIONS

JP application 2021-024572 filed Feb. 18, 2021—Office Action dated Apr. 6, 2022, Machine Translation, Apr. 7, 2022; 9 pages.

* cited by examiner

US 11,469,061 B2

CONTROL DEVICE SENSOR ROTATION

FIELD

Embodiments of the subject matter disclosed herein relate the field of control devices and, more particularly, to control device sensor rotation and controls for use in x-ray vascular examination and movement of medical imaging and diagnostic sensor equipment in relation to an examination subject.

BACKGROUND

Cardiovascular imaging systems that offers clinicians advanced image quality, innovative dose management, and easy patient positioning are desired. Few available systems meet all clinical needs for interventional and diagnostic angiography procedures, provide consistently high imaging performance, and provide the medical practitioner operating the system with easy to use, practical, and effective controls. Moreover, such cardiovascular imaging systems are complex and typically comprise numerous components requiring monitoring and control. Typical components of such a system may include, for example, an x-ray high-frequency and high-voltage generator, an x-ray tube and collimator, an image detection unit, various in-room and control monitors, an external chiller for providing continuous water cooling, ceiling and table mounted radiation protection for shielding the patient and the medical practitioner/technician/user of the imaging system, and a floor mounted gantry with an offset c-arm that may be repositioned, along with movement of a repositionable patient table, to achieve multiple angles and relationships between a target object to be examined (of the patient being examined) and particular components of the imaging system.

Desirable features of an imaging system include various controls via a control cabinet and/or one or more table-side control box, an easily repositionable patient table, and one or more display associated with the operation of the several components of the imaging system. A particular machine might include, for example, an angio table with "floating top" design for flexible patient positioning. The table height may range between, for example, approximately 30 inches to approximately 43 inches, and may include a table side user interface (TSUI), a table side status control (TSSC), and one or more controls for repositioning the top of the table relative to its position on the floor and/or relative to its position with respect to the c-arm or other imaging or testing components.

Conventional controls may include, for example, one or more touch screen, an exposure hand switch, one or more push-to-select or toggle type buttons, one or more mouse type controller, a console keyboard and mouse, one or more joy-stick type controller, one or more on-floor positioned foot switch, and/or one or more rotary knob. Each of these types of controls offers advantages and disadvantages in terms of ease of use, conformance to natural operator (medical practitioner) hand motion, capabilities enabling the operator to use the controls to follow anatomical features of the patient or target object being examined, and mechanical features for permitting a desired controlled response while preventing undesirable response.

A hand-rotative mechanical control such as, for example, a rotary knob, is desirable for initiating a controlled intended motion in one or more components of the imaging system in response to the operator rotating the knob. Existing designs, however, may not provide sufficient accuracy of control or sufficiently prevent unintended motion in the one or more components to be controlled. Improvements in such a control device are therefore desirable.

BRIEF DESCRIPTION

In one aspect, the present disclosure is directed to an exemplary embodiment of a control device which allows an operator/user to follow the user's anatomical movement by following natural hand rotation, includes two independent detection sensors or sensor portions embedded in two different parts of the device, one in a fixed part and one in a mobile or rotative part, with resistance to mutual disturbance between the two, the device comprising: a knob portion rotatable about a first axis of rotation; at least one sensor configured to sense a rotational position of the knob in relation to the first axis of rotation; circuitry adapted to at least provide electrical power to the rotative knob portion; circuitry adapted to transmit the sensed rotational position of the knob; and a base portion rotatably coupled to the knob portion, the base portion having a fixed position in relation to the first axis of rotation.

In one aspect, the device further comprises a cam portion having a cylindrical wedge shape and a follower portion, the cam portion and follower portion having between them a position of maximum potential energy and a position of equilibrium, whereby the follower portion engages with the cam portion as the knob is rotated about the first axis to move between the maximum potential and equilibrium positions.

In one aspect, the follower and cam are in a more compressed state near the position of maximum potential and a less compressed state near the position of equilibrium, and the follower includes a spring urging it toward the cam so that the knob registers to an initial position.

In one aspect, the follower comprises a ball at its far end that engages with a surface of the cam, the ball configured to enable linear motion of the follower in a direction parallel with the first axis as the ball and follower move rotatively in relation to the cam about the first axis without disturbing motion in a plane perpendicular to the first axis so as to avoid disturbing a sensor or sensor portion not positioned in the rotative part of the control device.

In one aspect, the rotation of the knob in one direction moves the follower from the position of equilibrium to the position of maximum potential and then back again to the position of equilibrium.

In one aspect, the sensed rotational position of the knob is determined by the at least one sensor configured to sense a linear position of the follower, the linear position being parallel to the first axis.

In one aspect, the device further comprises a cam portion and two follower portions, the cam portion and follower portions having between them a position of maximum potential energy and a position of equilibrium, whereby each follower portion engages with the cam portion as the knob is rotated about the first axis to move between the maximum potential and equilibrium positions.

In one aspect, each follower is in a more compressed state near the position of maximum potential and a less compressed state near the position of equilibrium, and the cam portion includes a spring urging it toward the followers so that the knob registers to an initial position.

In one aspect, each follower comprises a ball at its far end that engages with a surface of the cam, the ball configured to enable linear motion of the cam in a direction parallel with the first axis as the ball and follower move in rotative relation to the cam about the first axis without disturbing motion in a plane perpendicular to the first axis so as to avoid disturbing a sensor or sensor portion not positioned in the rotative part of the control device.

In one aspect, rotation of the knob in one direction moves the followers from the position of equilibrium to the position of maximum potential, and subsequent rotation of the knob in the opposite direction moves each follower from the position of maximum potential to the position of equilibrium.

In one aspect, the cam is symmetrical about a median plane extending along and including the first axis.

In one aspect, the median plane intersects each follower so that the two followers are opposite one another with the first axis extending therebetween.

In one aspect, the cam includes radially angled cam surfaces so that increasing a spring force of the spring of the cam portion provides increased compression between the two followers and the cam, increased anti-backlash between the rotative portion and the fixed portion of the control device, and/or higher torque required for rotation of the knob in relation to the base.

In one aspect, the control device comprises at least one electrical cable interconnecting circuitry located within the rotative part and circuitry located with the fixed part, with the electrical cable routed through respective openings in the rotative and fixed parts extending along the axis of rotation of the knob.

In one aspect, the device further comprises a circuit board attached to the rotative knob portion that is perpendicular to and extending around the first axis.

In one aspect, the at least one sensor comprises at least one rolling pogo pin for engagement with the circuit board, wherein the circuit board comprises a target surface for an electrical contact end of a plunger portion of the pogo pin, the plunger portion retractable into a barrel portion of the pogo pin and having a spring associated therewith for urging the plunger to extend from the barrel in a direction toward the electrical contact end and contact with the target surface of the circuit board.

In one aspect, a rotational position of the at least one rolling pogo pin in relation to the circuit board determines the sensed rotational position of the knob.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of systems and methods for a control device which allows an operator/user to follow the user's anatomical movement by following natural hand rotation, between two independent detection sensors or sensor portions embedded in two different parts of the device, one in a fixed part and one in a mobile or rotative part without mutual disturbance. The device comprises a knob portion rotatable about a first axis of rotation; at least one sensor configured to sense a rotational position of the knob in relation to the first axis of rotation; circuitry adapted to transmit the sensed rotational position of the knob; and a base portion rotatably coupled to the knob portion, the base portion having a fixed position in relation to the first axis of rotation.

Figure 1:
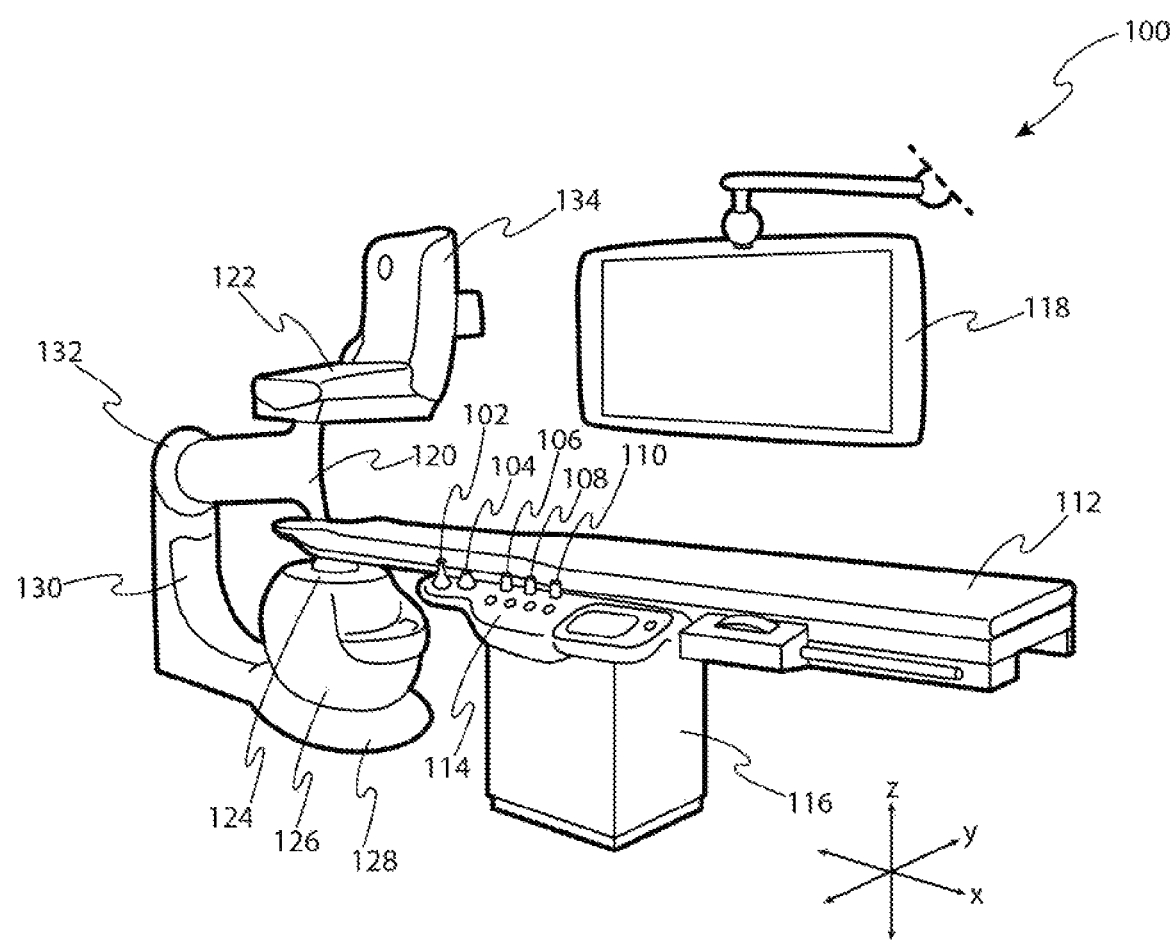
FIG. 1 is an exemplary medical imaging and diagnostic system including rotational control device sensors.

Although the embodiments described are presented in the context of one or more rotary control knob used with a medical imaging and diagnostic system (as shown in FIG. 1), the embodiments and inventive features described may be used in other systems, with other types of devices and systems, and in other, non-medical applications. For instance, embodiments described may be used in manufacturing or industrial applications, for providing control signals to a system whereby the control signals are generated in response to movement of a rotary control device or rotary control knob.

Figure 3A:
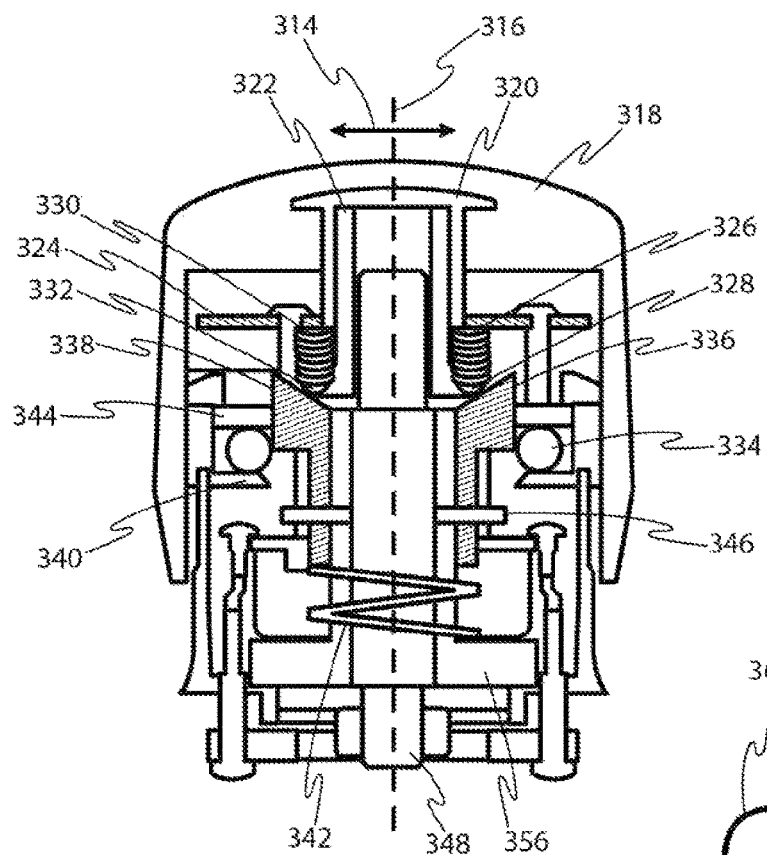
FIG. 3A illustrates a cut view of a rotational control knob with a cam, two followers, and at least one sensor or sensor portion, according to embodiments.
Figure 3B:
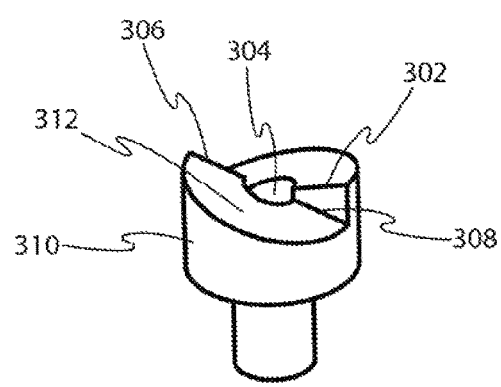
FIG. 3B illustrates a perspective view of an exemplary cam component of the rotational control knob shown in FIG. 3A.
Figure 4A:
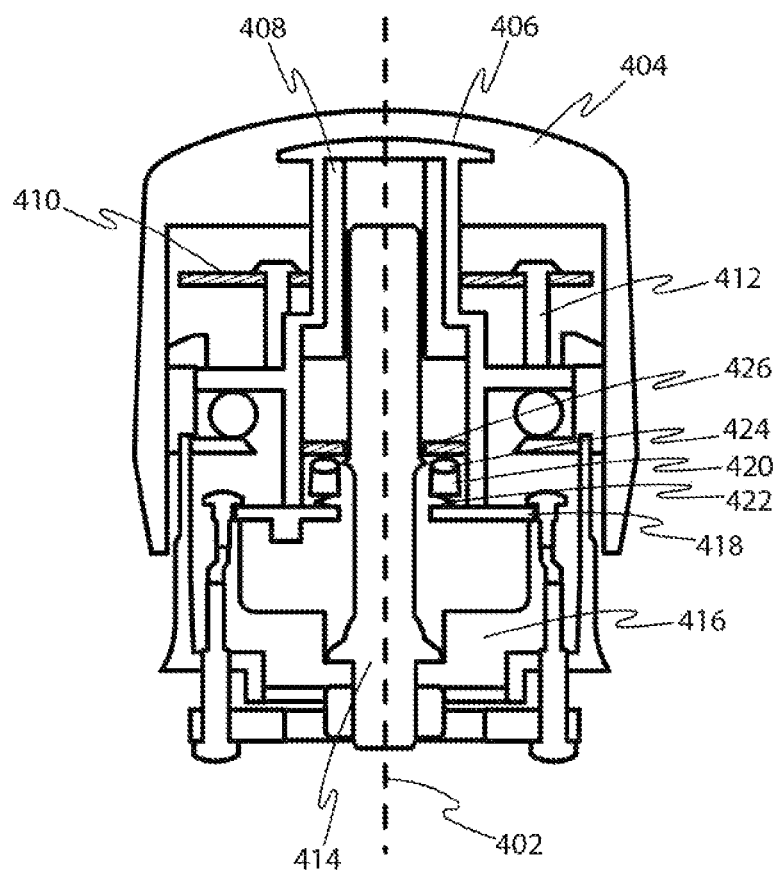
FIG. 4A illustrates cut view of a rotational control knob with at least one circuit board and a rolling pogo pin for sensing the rotational position of the knob, according to embodiments.
Figure 4B:
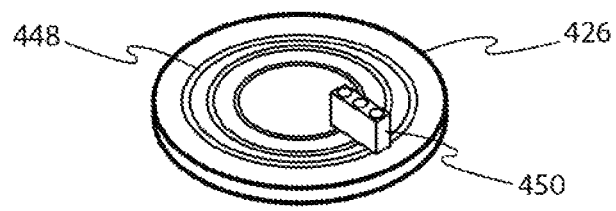
FIG. 4B illustrates a perspective view of an exemplary circuit board component of the rotational control knob shown in FIG. 4A.

As an overview, FIG. 1 depicts an exemplary system having one or more rotational control devices, and FIGS. 2A, 2B, 2C, and 2D provide details of an exemplary rotary control knob having a cam and follower. FIGS. 3A, 3B, and 3D provide details of an exemplary rotary control knob having a cam configured for use with two followers. And FIGS. 4A and 4B provide details of an exemplary rotary control knob having a circular disc-shaped circuit board on which the position of the rotary knob is determined.

FIG. 1 is an exemplary medical imaging and diagnostic system 100 including rotational control device sensors. Components of the exemplary system 100 may include an x-ray high-frequency and high-voltage generator (for example, housed in a lower unit 126), an x-ray tube and collimator (for example, housed in the lower unit emitter 126, 124), an image detection unit 122, various in-room and control monitors (for example, controls display/touchscreen 136 and display 118), an external chiller for providing continuous water cooling (not shown), ceiling and table mounted radiation protection for shielding the patient and the medical practitioner/technician/user of the imaging system (not all shown or explicitly referenced), and a floor mounted gantry 130 with an offset c-arm 120 that may be repositioned, along with movement of a repositionable patient table 112, to achieve multiple angles and relationships between a target object to be examined (of the patient being examined) and particular components of the imaging system. The c-arm 120 supports an upper unit 134 (with the detector 122) and the lower unit 126 (with emitter 124) so that the lower unit 126 and upper unit 134 may be rotated opposite one another about at least a portion of the patient table 112. For example, the gantry 130 includes a floor standing portion 128 and a pivot point 132, with the pivot point 132 allowing for rotating the emitter 124 and detector 122 about a rotational axis at (or running through) the pivot point 132 and defining a longitudinal axis of rotation (or x-axis of rotation) that, as illustrated in FIG. 1, extends along the length of the patient table 112. The offset c-arm 120 may further comprise slidably repositionable tracks allowing for rotating the emitter 124 and detector 122 about a rotation axis that is perpendicular to the longitudinal axis (defining a transverse or y-axis axis of rotation), thereby, allowing the emitter 124 and detector 122 to be rotatably repositioned along one or both of two perpendicular axis of rotation (i.e. one or both of the x-axis and y-axis of rotation) about at least a portion of the table 112.

The table 112, as shown, rests upon a floor standing lower cabinet 116, which may house, if not located elsewhere, one or more computer processor, computer memory/storage, circuitry adapted to receive and transmit signals from wired or wireless components of the system 100, power supply electronics, and/or other components not expressly shown or described further herein that may be needed for the system 100. The lower cabinet 116 may, for example, house electronics and circuitry interconnecting one or more of the controls 102, 104, 106, 108, 110 with electric motors arranged for controllably repositioning the table 112 with respect to the lower cabinet 116, and/or controllably repositioning the table 112 with respect to other components of the system 100 such as, for example, the emitter 124 and detector 122. The table 112 may, for example, be repositionable longitudinally in a direction toward or away from the gantry 130 and along the aforementioned longitudinal axis running along the length of the table 112. The table 112 may be, for example, raised or lowered vertically, moved in a transverse direction (perpendicular to the longitudinal axis), and/or rotated away from its longitudinal alignment (as shown in FIG. 1) with the rotational axis of the c-arm 120. For example, the table 112 may be rotated, about a vertical or z-axis of rotation, out of the alignment shown in FIG. 1 to positions between a zero or longitudinally aligned position and a position that is rotated 180 degrees.

In some embodiments, the one or more rotary controls comprise one or more table side controls 102, 104, 106, 108, 110 positioned within a control panel 114 for controlling operational aspects of the system, such as repositioning the patient table 112 or another one or more of the components of the system 100. During operation of system 100, a patient may be positioned upon the table 112, and the table 112 may be moved longitudinally and/or transversely and/or rotated about a vertical/z-axis via hand rotation of mechanical controls such as one or more rotary controls 102, 104, 106, 108, 110 by a medical practitioner/user of the system. Further, one or more rotary controls 102, 104, 106, 108, 110 may be hand rotated to reposition the c-arm 120 (or emitter 124 and detector 122) about a longitudinal/x-axis and/or a transverse/y-axis.

Figure 2A:
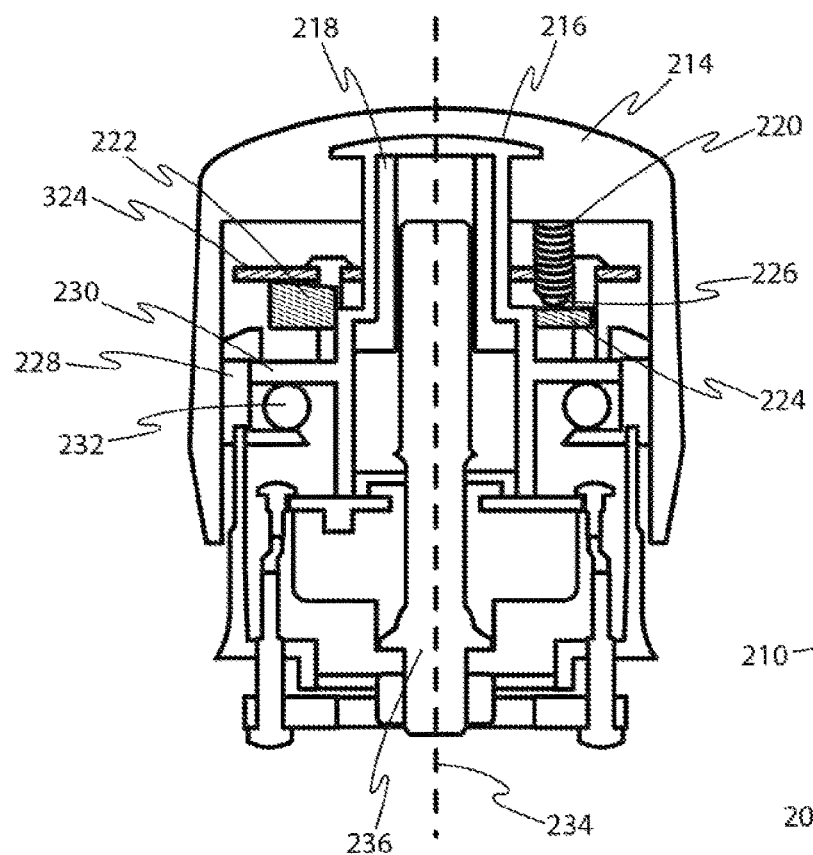
FIG. 2A illustrates a cut view of a rotational control knob with a cam, a follower, and at least one sensor or sensor portion, according to embodiments.

FIG. 2A illustrates a cut view of an exemplary rotational mechanical control knob having a cam 222, 224, a follower 220, and a sensor positioned within a rotative portion 214 of the rotary knob, according to embodiments. The cam may comprise a cylindrical wedge (or angle-cut cylinder section) with a hollow center and upward facing ramp portion, as shown and described in more detail in FIG. 2B. In the cut view shown in FIG. 2A, the cam portion 222 shown to the left of the axis of rotation 234 has a greater height than the cam portion 224 shown to the right of the axis of rotation 234. The upper surface of the cam portion 224 engages a ball 224 which rides along the surface of the cam as the rotative portion 214 of the control knob is moved about its axis of rotation 234. The ball 224 may be pushed against the cam surface by a spring or plunger affixed to the rotative portion 214, with the ball and spring/plunger comprising a follower 220 that translates the change in height of the cam as it rotates to a linear motion. The linear motion or position of the follower, or relative length of the follower between the cam surface and rotative portion 214, is sensed by a sensor, such as sensor 246 described in more detail with respect to FIGS. 2C and 2D, and coupled with circuitry adapted to transmit the sensor output signal (or the sensed rotational position of the knob associated with the sensor output signal) to, for example, circuitry corresponding to one or more components of the system 100 for initiating a controlled intended motion in response to an operator rotating the control knob.

In some embodiments, the rotary control device may comprise at least one capacitive antenna, and/or one or more sensor coupled with circuitry adapted to provide proximity sensing, and/or circuitry associated with either or both of the one or more capacitive antenna and one or more sensor/proximity sensor (hereinafter, referred to collectively, for simplicity, as "proximity sensor" or "capacitive antenna"). The capacitive antenna, proximity sensor, and circuitry therefor, may comprise a circuit board (for example circuit board 324) or separate elements, and are part of the rotative portion of the rotary control device, such as rotative portion 214; and may be integral with one another. Further, the aforementioned proximity sensor circuitry may be combined with and integral to circuitry and circuit board elements comprising the sensor or sensors or sensor portions associated with sensing the position of the rotative portion with respect to the fixed or non-rotative portion, except that the proximity sensor and (rotative portion) position sensor, such as sensor 246, are considered independent from one another and are (desirably) free from mutual disturbance between one another. In some embodiments, a proximity sensor may be positioned within the rotative portion of the rotary control device, such as near an outward most surface of the rotary knob, and oriented and configured so as to provide proximity sensing of, for example, a patient or operator/user position in relation to the rotary control device. In some embodiments, the proximity sensor performs proximity detection more effectively having at least some of the electronics and circuitry, and electric/electrical power therefor, that are needed for the capacitive antenna/proximity sensor, housed within the rotative portion of the rotary control device.

The rotative portion 214, as shown in FIG. 2A, includes rotative portions that may be rotatably moved about (or rotated about) an axis of rotation 234. Rotative mechanical structure may include the portion 214 comprising an outward most or exterior rotary control knob surface, an associated rotary knob sleeve 216 for engagement of the outward most knob portion to an inner sleeve 218. One or more bearing 232, or alternatively a sealing ring 232, may be used, for example, for providing an interface between rotative parts and fixed parts of the control device. For example, non-rotative intermediate structure 230 and rotative structure 228 may capture or envelope the bearing/seal 232. Also, an inner shaft 236 may be fixably attached, as shown, to fixed parts of the control device, extending from a base portion upward along the axis 234. The rotative portion 214 (and inner sleeve 218) may then fit over the upper end of the inner shaft, forming a rotative coupling between the two.

Figure 2B:
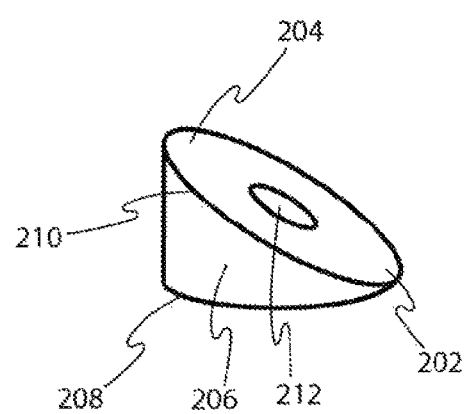
FIG. 2B illustrates a perspective view of an exemplary cam component of the rotational control knob shown in FIG. 2A.

FIG. 2B illustrates a perspective view of an exemplary cam component of the rotational control knob shown in FIG. 2A. The cam comprises a cylindrical wedge or angle-cut cylinder 206 having a hollow center 212 extending along an axis of rotation. The cam includes sides extending from a circular base 208 to an angle-cut edge 210. A maximum height portion 204 comprises a position where the follower 226 has a maximum potential energy because the follower is in a most compressed state (at what may be referred to as maximum potential energy position of the control knob). A minimum height portion 202 comprises a position where the follower 226 has a minimum potential energy because the follower 226 is in at least compressed state (at what may be referred to as an equilibrium position of the control knob). A line extending between the equilibrium position 202 and the maximum potential energy position 204 defines a major axis of the cylindrical wedge, with the segment perpendicular to the major axis extending between respective sides of the angle-cut edge 210 defines a minor axis of the cylindrical wedge.

Figure 2C:
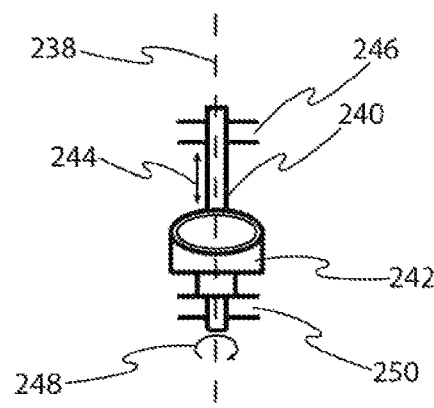
FIG. 2C illustrates a diagrammatic side view of an exemplary cam and follower as in FIG. 2A.
Figure 2D:
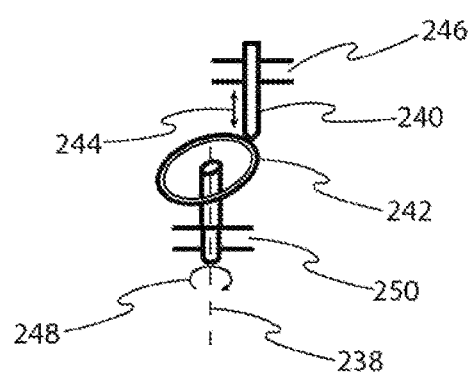
FIG. 2D illustrates the diagrammatic side view shown in FIG. 2C rotated 90 degrees about an axis of rotation.

FIG. 2C illustrates a diagrammatic side view of an exemplary cam and follower as in FIG. 2A, and FIG. 2D illustrates the diagrammatic side view shown in FIG. 2C rotated 90 degrees about an axis of rotation 238. In some embodiments, the control device includes a cylindrical wedge shaped cam 242 which is centered about an axis of rotation 238 and provides an upper surface upon which at least one follower 240 may slide as the follower moves along with the rotative portion 214 of the knob. The follower 240 is part of the rotative portion 214 and is configured so as to move in a vertical linear motion 244, and a sensor 246 is used within the rotative portion of the control device to sense a position of the follower, and/or a relative length of the follower, and/or a movement of the follower, which corresponds to a height of the cam and a sensed rotational position of the rotative portion. The sensor 246 may comprise a linear sensor, a Hall Effect sensor, magneto-resistive sensor, an optical sensor, or other type of sensor.

In FIGS. 2A, 2B, 2C, and 2D both the follower 240 and sensor 246 are part of the rotative structure of the rotary control knob, and the cam 242 is part of the fixed portion 250 that does not rotate about the axis 238. The rotation indication 248 illustrated in FIGS. 2C and 2D depict the rotation of the rotative part comprising the sensor 246 and follower 240 about the axis of rotation 238. In some embodiments, the rotary control knob has a "return to zero" or equilibrium position where the rotative part returns to when a rotative force is not being applied to the rotative part. The equilibrium position is, as described above, the point where the follower is at its most uncompressed state, which is when the follower is at the minimum height position 202 of the cam. When a rotative force is applied to the rotary knob to move the ramp surface of the cam in relation to the follower, the follower spring/plunger becomes compressed until the follower is located at the maximum potential energy position 204. Thereafter, the rotative part will be rotatably self driven to move toward the equilibrium (lowest potential energy) position 202. If the rotative part is urged just beyond the maximum potential energy position, the rotative part will be rotatably self driven to continue in the same direction of rotation toward the equilibrium position. If the rotative part is released just before the maximum potential energy position, the rotative part will be rotatably self driven to return to the equilibrium (or zero) position. In this way, the rotary control device includes a spring effect which registers to an initial (equilibrium or zero) position. The spring effect, which is acting in a direction parallel with the axis of rotation of the knob, may further provide resistance to lateral motion or motion that is perpendicular to or non-parallel with the axis of rotation of the knob.

As described with respect to FIGS. 2A, 2B, 2C, and 2D, rotative force exerted upon the rotative portion 214 causes the ball 224 to slide (or track) along the upper surface of the cam 242 to vary the compression of the follower, or vary the relative length of the follower, allowing for a sensor, such as sensor 246, to detect a linear position, or change in linear position, of the follower, such as follower 240. The sensor, which is sensitive to linear position along a vertical axis (or axis parallel with the axis of rotation 234), is therefore sensitive in a direction of motion parallel to the axis of rotation 234 and effectively insulated or less sensitive as to motion perpendicular to the axis of rotation 234. In this way, the rotary control device includes resistance (insensitivity) to motion or displacement that is perpendicular to its axis of rotation and/or resistance (insensitivity) to motion or displacement that is not parallel to its axis of rotation, such as axis of rotation 234.

In the context of a system, such as system 100, where the rotary control device may comprise, for example, rotary control 102, and the patient table 112 is oriented as shown in FIG. 1 and incorporates a push-to-enable type sensing configuration whereby the table may be repositioned horizontally, whether longitudinally (along an x-axis, toward or away from the c-arm), transversely (which may also be referred to as laterally, along a y-axis, away from or toward the table side controls), and/or rotatably (about a z-axis), by the operator/user pushing the table in a desired horizontal orientation in order to reposition the table, one or more horizontal motion sensor or sensor portion may be located within a fixed part/portion of the system, such the table side controls or positionally fixed portions of the table. The one or more horizontal motion sensor or sensor portion may be susceptible to false or inaccurate sensing with disturbance in the horizontal plane. That is, such horizontal sensing, which may include sensor components within fixed portions of the system, may be unfavorably affected by motion in the horizontal plane. The rotary control device, however, as described for some embodiments, includes resistance (insensitivity) to motion or displacement that is not parallel to its axis of rotation, such as axis of rotation 234; and when such rotary control device is positioned and oriented with its axis of rotation so as not to be parallel with the aforementioned horizontal plane, the rotary control device includes resistance (insensitivity) to horizontal motion. In other words, the rotary control device in some embodiments provides, in its operation, an ability to control one or more components of the system, such as system 100, without disturbing horizontal motion which may activate a sensor sensitive to such motion, and without operation of the rotary control device itself being susceptible to horizontal motion. For example, a rotary control device as described in FIGS. 2A, 2B, 2C, and 2D, may be used to control rotation of the c-arm 120 about the x-axis (longitudinal axis) so as to permit fine/accurate orientation of the emitter 124 and detector 122 in relation to a patient positioned on the patient table 112, with operation of the rotary control device comprising for example rotary control 102, without being effected by horizontal motion (motion in the x-y plane) and without affecting horizontal motion by, for instance, triggering actuation of a push-to-enable lateral/transverse (y-axis direction) repositioning of the table 112.

FIGS. 2A, 2B, 2C, and 2D, as described, illustrate a control device which allows an operator/user to follow the user's anatomical movement by following natural hand rotation, includes two independent detection sensors or sensor portions embedded in two different parts of the device, one in a fixed part and one in a mobile or rotative part, with resistance to mutual disturbance between the two, the device comprising: a knob portion rotatable about a first axis of rotation; at least one sensor configured to sense a rotational position of the knob in relation to the first axis of rotation; circuitry adapted to at least provide electrical power to the rotative knob portion; circuitry adapted to transmit the sensed rotational position of the knob; and a base portion rotatably coupled to the knob portion, the base portion having a fixed position in relation to the first axis of rotation.

In one aspect, the device further comprises a cam portion having a cylindrical wedge shape and a follower portion, the cam portion and follower portion having between them a position of maximum potential energy and a position of equilibrium, whereby the follower portion engages with the cam portion as the knob is rotated about the first axis to move between the maximum potential and equilibrium positions.

In one aspect, the follower and cam are in a more compressed state near the position of maximum potential and a less compressed state near the position of equilibrium, and the follower includes a spring urging it toward the cam so that the knob registers to an initial position.

In one aspect, the follower comprises a ball at its far end that engages with a surface of the cam, the ball configured to enable linear motion of the follower in a direction parallel with the first axis as the ball and follower move rotatively in relation to the cam about the first axis without disturbing motion in a plane perpendicular to the first axis so as to avoid disturbing a sensor or sensor portion not positioned in the rotative part of the control device.

In one aspect, the rotation of the knob in one direction moves the follower from the position of equilibrium to the position of maximum potential and then back again to the position of equilibrium.

In one aspect, the sensed rotational position of the knob is determined by the at least one sensor configured to sense a linear position of the follower, the linear position being parallel to the first axis.

Next, FIG. 3A illustrates a cut view of an exemplary rotational control knob with a cam 338, 336, two followers 330 and 326, and at least one sensor or sensor portion, such as circuit board 324, positioned within a rotative portion 318. As shown, the rotative part 318 may rotate about an axis of rotation 316. As the rotative part moves, each ball 332 and 328 attached to the far end of respective followers 330 and 326 slides (or rolls) along the upper surface (track) of the cam 338, 336, and the cam is then pushed according to changes in cam height in a direction downward along the axis of rotation 316 against a compression spring or spring washers 342 that presses against a lower base portion 356 that is attached to or part of a fixed portion of the rotary control device. In this way, the change in cam height as the rotative part is rotated about the axis of rotation is translated into a linear motion of the cam.

Components comprising the rotative portion of the control device illustrated in FIG. 3A (and FIG. 4A) may be substantially similar and/or the same as similarly illustrated and/or positioned components as illustrated and described for FIG. 2A. The rotative portion 318, as shown in FIG. 3A, includes rotative portions that may be rotatably moved about (or rotated about) an axis of rotation 316. Rotative mechanical structure may include the portion 318 comprising an outward most or exterior rotary control knob surface, an associated rotary knob sleeve 320 for engagement of the outward most knob portion to an inner sleeve 322. One or more bearing 334, or alternatively a sealing ring 334, may be used, for example, for providing an interface between rotative parts and fixed parts of the control device. For example, non-rotative intermediate structure 344 and rotative structure 340 may capture or envelope the bearing/seal 334. Further, an inner shaft 348 may be fixably attached, as shown, to fixed parts of the control device, extending from a base portion, such as lower base portion 356, upward along the axis 316. The rotative portion 318 (and inner sleeve 322) may then fit over the upper end of the inner shaft, forming a rotative coupling between the two.

FIG. 3B illustrates a perspective view of an exemplary cam component of the rotational control knob shown in FIG. 3A. The cam comprises an upper cylinder portion having a top comprising two upward facing surfaces (tracks), such as surface (track) 312, which are symmetric to one another about a hollow center 304 extending along an axis of rotation. The upper cylinder portion may be described as identical halves of a cylindrical wedge or angle-cut cylinder, with each half joined together with one another. The resulting upper surfaces provide two tracks, each comprising 180 degrees of the upper (top) surface of the upper cylinder portion. Each track comprises a maximum height portion having a position 306, 302 where a respective follower 330, 326 (ball 332, 328) and cam track surface has a maximum potential energy because the compression spring 342 is in a most compressed state (at what may be referred to as maximum potential energy position of the control knob). Each track further comprises a minimum height portion having a position, such as position 308, where a respective follower 330, 326 (ball 332, 328) and cam track surface has a minimum potential energy because the compression spring 342 is in at least compressed state (at what may be referred to as an equilibrium or zero or starting position of the control knob). A line extending through the zero position 308 and the maximum potential energy position 306 defines a major axis of each cylindrical wedge half. Further, as shown, the upper cylinder portion comprising the aforementioned tracks may have an axially aligned smaller diameter cylinder or pedestal opposite the cam tracks, with the hollow center 304 extending from the cam track surfaces downward through the pedestal.

Also as shown in FIG. 3B, each of the two cam tracks, such as cam track 312, provides for a follower to move in a first direction along the track from a point of maximum potential energy, such as position 306, to a point of minimum potential energy, such as position 308, whereafter further rotation in the first direction is mechanically stopped (with a hard stop) due to the sheer edge transition, such as the sheer edge between points 308 and 302, where the two symmetric cam halves join together. Movement in the first direction, that is from the point of maximum potential energy to the point of minimum potential energy, is aided by the compression spring pushing the cam surfaces toward the followers. In this way, a return to zero or return to start capability is provided. In other words, rotative force may be applied to move the followers toward the point of maximum potential energy (for each follower), with the compression spring and ramp orientation of the cam urging the followers to move the other way, urging counterrotation of the rotative part back toward the starting point, and ultimately returning the followers to the starting point or a point of minimum rotation when rotative forces on the rotative portion are removed.

Figure 3C:
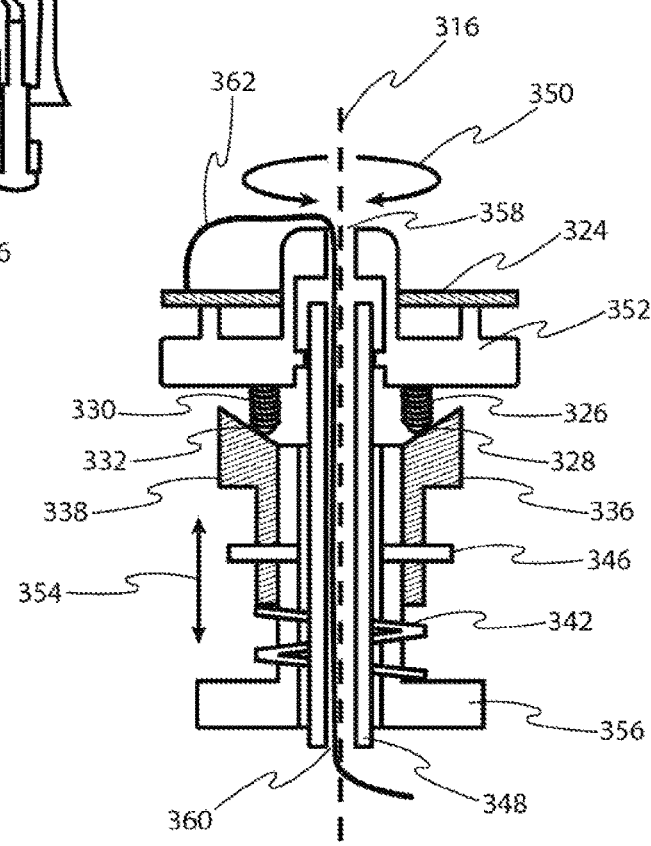
FIG. 3C illustrates a diagrammatic sectional side view of exemplary cam and follower components as in FIG. 3A.

FIG. 3C illustrates a diagrammatic sectional side view of the exemplary cam and follower as in FIG. 3A as viewed at a median plan running through an axis of rotation 316. As shown, electrical wiring, such as an electrical cable 362, extends from a circuit board, such as circuit board 324, embedded within the rotative portion, through an opening, such as hole or aperture 358, in the rotative cap running along the axis of rotation and continuing downward through an opening, such as hole or aperture 360, running through the inner shaft along the axis of rotation. In this way, electrical wiring, for providing at least electrical power circuitry and circuit board within the rotative portion, extends between the fixed and rotative portions of the control device.

The rotation indication 350 illustrated in FIG. 3C depicts the rotation of the rotative part comprising the rotating circuit board and the followers 330 and 326 about the axis of rotation 316. As the rotative part rotates, the ball at each end of each follower moves along the cam track surfaces, with changes in the (symmetric) cam height causing a linear movement, such as movement 354, of the cam in an axial direction. As illustrated, the cam 336 moves axially (linearly) between fixed length followers 330, 328 and the lower base portion 356. The compression spring 342 urges the cam 336 toward the followers to maintain contact between the cam track and followers. In some embodiments, a pin 346 may be used, to rotationally lock the cam 336 and a sleeve portion of the lower base portion 356 that extends axially upward, and still allow axial (linear) movement of the cam. In some embodiments, the pin 346 comprises a sensor, such as a linear sensor or sensor 246 as previously described, adapted to sense an axial (linear) position of the (axially moveable) cam 336 in relation to the (fixed) lower base portion 356. In other embodiments, the sensor is located within the rotative portion 352 and is adapted and oriented so as to detect a linear position of an axial reference point on the cam 336 that corresponds to a height of the cam 336; as the follower moves along the cam track, the sensor detects the change in axial position of the axial reference point.

As described with respect to FIGS. 3A, 3B, and 3D, rotative force exerted upon the rotative portion 318 causes each of the two followers 330 and 326 to slide (or track) along respective upper surfaces (tracks) of the cam 338, 328 to vary the amount of compression of the compression spring 342 as the cam moves linearly in an axial direction along the axis of rotation 316. The cam upper (track) surfaces are symmetric so that each follower contacts the cam at an area where the cam height is the same for each follower, thereby providing additional balance and symmetry in the forces exerted axially, on both sides of the axis of rotation 316 and at the same distance from the axis of rotation. Further, as shown more clearly in FIGS. 3A and 3C, the cam upper (track) surfaces, as shown in side and section views for cam 338 and cam 336, may be angled radially, for example, angled as shown where the radially outward edge of the cam is higher or axially closer to the top of the rotative portion than the radially inward edge of the cam, and so that the two followers are effectively captured and urged radially inward, with capture forces acting radially inward toward the axis of rotation 316. In this way, the rotary control device includes resistance to displacement 314 in directions perpendicular to the axis of rotation and resistance to backlash or play in the mechanical operation of the rotative part in relation to the fixed part of the control device. Additionally, the amount of compressive force (or spring force) exerted by the compression spring 342 may be increased, such as by increasing a stiffness of the compressions spring, when a higher torque for the rotative portion is desired and/or when additional anti-backlash energy is desired.

FIGS. 3A, 3B, and 3C, as described, illustrate a control device which allows an operator/user to follow the user's anatomical movement by following natural hand rotation, includes two independent detection sensors or sensor portions embedded in two different parts of the device, one in a fixed part and one in a mobile or rotative part, with resistance to mutual disturbance between the two, the device comprising: a knob portion rotatable about a first axis of rotation; at least one sensor configured to sense a rotational position of the knob in relation to the first axis of rotation; circuitry adapted to at least provide electrical power to the rotative knob portion; circuitry adapted to transmit the sensed rotational position of the knob; and a base portion rotatably coupled to the knob portion, the base portion having a fixed position in relation to the first axis of rotation.

In one aspect, the device further comprises a cam portion and two follower portions, the cam portion and follower portions having between them a position of maximum potential energy and a position of equilibrium, whereby each follower portion engages with the cam portion as the knob is rotated about the first axis to move between the maximum potential and equilibrium positions.

In one aspect, each follower is in a more compressed state near the position of maximum potential and a less compressed state near the position of equilibrium, and the cam portion includes a spring urging it toward the followers so that the knob registers to an initial position.

In one aspect, each follower comprises a ball at its far end that engages with a surface of the cam, the ball configured to enable linear motion of the cam in a direction parallel with the first axis as the ball and follower move in rotative relation to the cam about the first axis without disturbing motion in a plane perpendicular to the first axis so as to avoid disturbing a sensor or sensor portion not positioned in the rotative part of the control device.

In one aspect, rotation of the knob in one direction moves the followers from the position of equilibrium to the position of maximum potential, and subsequent rotation of the knob in the opposite direction moves each follower from the position of maximum potential to the position of equilibrium.

In one aspect, the cam is symmetrical about a median plane extending along and including the first axis.

In one aspect, the median plane intersects each follower so that the two followers are opposite one another with the first axis extending therebetween.

In one aspect, the cam includes radially angled cam surfaces so that increasing a spring force of the spring of the cam portion provides increased compression between the two followers and the cam, increased anti-backlash between the rotative portion and the fixed portion of the control device, and/or higher torque required for rotation of the knob in relation to the base.

In one aspect, the control device comprises at least one electrical cable interconnecting circuitry located within the rotative part and circuitry located with the fixed part, with the electrical cable routed through respective openings in the rotative and fixed parts extending along the axis of rotation of the knob.

Turning now to FIGS. 4A and 4B, FIG. 4A illustrates cut view of a rotational control knob with circuit board and rolling pogo pin for sensing the rotational position of the knob, according to embodiments, and FIG. 4B illustrates a perspective view of an exemplary circuit board 426 component of the rotational control knob shown in FIG. 4A. In some embodiments, a disc-shaped or circular shaped printed circuit board 426 housed within and attached to a rotative portion 404 of the control device is centered about and perpendicular with a rotation of axis 402, and one or more rolling pogo pin 420 attached to a fixed part 418, 416 of the control device so as to mechanically contact the circuit board 426. In some embodiments, the pogo pins 420 are configured and adapted with circuitry to provide at least electrical power from the fixed part of the control device to the rotative portion of the control device, such as to circuitry within the rotative portion including circuit board 410. For example, as shown in FIG. 4B, the pogo pins may comprise a pogo pin module 450 comprising several individual pogo pin, with each individual pin, in cooperation with the circuit board 426, rotatably maintaining contact with a respective corresponding conductive track 448 so as to provide an electrical path between the fixed part of the control device and the rotative part of the control device. In some embodiments, the pins 420 and circuit board 426 provide electrical power and/or data from the fixed part to the rotative part of the control device. In this way, an electrical connection via mechanical contact between a pogo pin attached to a fixed part of the control device and a conductive path or element on a circuit board attached to a rotative portion of the control device, provides a "wireless" connection between the fixed part and the rotative part of the control device.

In order for sensing the rotation position of the knob, the circuit board may, for example, include resistive conductors or conductor patterns or optical elements, which, when contacted or read, such as by pins or sensor elements attached to the fixed part of the control device, provide a unique resistive or other electrical or optical reference for determination of the rotational position of the rotative part of the control device. Other types of encoders may be used for sensing the rotational position of the rotative portion in relation to the fixed part. In some embodiments, at least one sensor comprises at least one rolling pogo pin for engagement with the circuit board, with the circuit board providing a target surface for an electrical contact end of the pogo pin. The pogo pin 420 may comprise a plunger (with an electrical contact end 424) that is retractable into a barrel portion, and a spring 422 within the barrel urges the plunger to extend from the barrel in a direction toward the electrical contact end for contact with the target surface of the circuit board. In some embodiments, a rotational position of the at least one rolling pogo pin in relation to the circuit board determines the sensed rotational position of the knob.

Components comprising the rotative portion of the control device illustrated in FIG. 4A may be substantially similar and/or the same as similarly illustrated and/or positioned components as illustrated and described for FIGS. 2A and 3A. The rotative portion 404, as shown in FIG. 4A, includes rotative portions that may be rotatably moved about (or rotated about) an axis of rotation 402. Rotative mechanical structure may include the portion 404 comprising an outward most or exterior rotary control knob surface, an associated rotary knob sleeve 406 for engagement of the outward most knob portion to an inner sleeve 408. One or more bearing, or alternatively a sealing ring, may be used, for example, for providing an interface between rotative parts and fixed parts of the control device. Further, an inner shaft 414 may be fixably attached, as shown, to fixed parts of the control device, extending from a base portion, such as lower base portion 416, upward along the axis 402. The rotative portion 404 (and inner sleeve 408) may then fit over the upper end of the inner shaft, forming a rotative coupling between the two.

FIGS. 4A and 4B, as described, illustrate a control device which allows an operator/user to follow the user's anatomical movement by following natural hand rotation, includes two independent detection sensors or sensor portions embedded in two different parts of the device, one in a fixed part and one in a mobile or rotative part, with resistance to mutual disturbance between the two, the device comprising: a knob portion rotatable about a first axis of rotation; at least one sensor configured to sense a rotational position of the knob in relation to the first axis of rotation; circuitry adapted to at least provide electrical power to the rotative knob portion; circuitry adapted to transmit the sensed rotational position of the knob; and a base portion rotatably coupled to the knob portion, the base portion having a fixed position in relation to the first axis of rotation.

In one aspect, the device further comprises a circuit board attached to the rotative knob portion that is perpendicular to and extending around the first axis.

In one aspect, the at least one sensor comprises at least one rolling pogo pin for engagement with the circuit board, wherein the circuit board comprises a target surface for an electrical contact end of a plunger portion of the pogo pin, the plunger portion retractable into a barrel portion of the pogo pin and having a spring associated therewith for urging the plunger to extend from the barrel in a direction toward the electrical contact end and contact with the target surface of the circuit board.

In one aspect, a rotational position of the at least one rolling pogo pin in relation to the circuit board determines the sensed rotational position of the knob.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A control device which allows an operator/user to follow the user's anatomical movement by following natural hand rotation, and includes two independent detection sensors or sensor portions embedded in two different parts of the device, one in a fixed part and one in a mobile or rotative part, with resistance to mutual disturbance between them, the device comprising:
   a knob portion rotatable about a first axis of rotation;
   at least one sensor configured to sense a rotational position of the knob in relation to the first axis of rotation;
   circuitry adapted to at least provide electrical power to the rotative knob portion;
   circuitry adapted to transmit the sensed rotational position of the knob;
   a base portion rotatably coupled to the knob portion, the base portion having a fixed position in relation to the first axis of rotation; and
   a cam portion and follower portions, whereby each follower portion engages with the cam portion as the knob is rotated about the first axis, wherein the cam portion and follower portions have between them a position of maximum potential energy and a position of equilibrium, whereby each follower portion engages with the cam portion as the knob is rotated about the first axis to move between the maximum potential and equilibrium positions.

2. The device of claim 1, wherein each follower is in a more compressed state near the position of maximum potential and a less compressed state near the position of equilibrium, and the cam portion includes a spring urging it toward the followers so that the knob registers to an initial position.

3. The device of claim 2, wherein each follower comprises a ball at a far end that engages with a surface of the cam, the ball configured to enable linear motion of the cam in a direction parallel with the first axis as the ball and follower move in rotative relation to the cam about the first axis without disturbing motion in a plane perpendicular to the first axis so as to avoid disturbing a sensor or sensor portion not positioned in the rotative part of the control device.

4. The device of claim 2, wherein rotation of the knob in one direction moves the followers from the position of equilibrium to the position of maximum potential, and subsequent rotation of the knob in the opposite direction moves each follower from the position of maximum potential to the position of equilibrium.

5. The device of claim 4, wherein the cam is symmetrical about a median plane extending along and including the first axis.

6. The device of claim 5, wherein the median plane intersects each follower so that the two followers are opposite one another with the first axis extending therebetween.

7. The device of claim 6, wherein the cam includes radially angled cam surfaces so that increasing a spring force of the spring of the cam portion provides increased compression between the two followers and the cam, increased anti-backlash between the rotative portion and the fixed portion of the control device, and/or higher torque required for rotation of the knob in relation to the base.

8. The device of claim 3, wherein rotation of the knob in one direction moves the followers from the position of equilibrium to the position of maximum potential, subsequent rotation of the knob in the opposite direction moves each follower from the position of maximum potential to the position of equilibrium, and further rotation in the opposite direction is mechanically prevented by a height transition in the cam blocking further rotation of each follower.

9. The device of claim 4, wherein rotation of the knob is self driven toward the equilibrium position such that the knob rotates toward the equilibrium position without rotative forces being applied to the rotative part by the operator/user.

10. A control device which allows an operator/user to follow the user's anatomical movement by following natural hand rotation, and includes two independent detection sensors or sensor portions embedded in two different parts of the device, one in a fixed part and one in a mobile or rotative part, with resistance to mutual disturbance between the two, the device comprising:
    a knob portion rotatable about a first axis of rotation;
    at least one sensor configured to sense a rotational position of the knob in relation to the first axis of rotation;
    circuitry adapted to at least provide electrical power to the rotative knob portion;
    circuitry adapted to transmit the sensed rotational position of the knob;
    a base portion rotatably coupled to the knob portion, the base portion having a fixed position in relation to the first axis of rotation; and
    at least one electrical cable interconnecting circuitry located within the rotative part and circuitry located with the fixed part, with the electrical cable routed through respective openings in the rotative and fixed parts extending along the axis of rotation of the knob.

11. The device of claim 10, wherein the cam portion and follower portions have between them a position of maximum potential energy and a position of equilibrium, whereby each follower portion engages with the cam portion as the knob is rotated about the first axis to move between the maximum potential and equilibrium positions, wherein each follower is in a more compressed state near the position of maximum potential and a less compressed state near the position of equilibrium, and the cam portion includes a spring urging it toward the followers so that the knob registers to an initial position, wherein each follower comprises a ball at a far end that engages with a surface of the cam, the ball configured to enable linear motion of the cam in a direction parallel with the first axis as the ball and follower move in rotative relation to the cam about the first axis without disturbing motion in a plane perpendicular to the first axis so as to avoid disturbing a sensor or sensor portion not positioned in the rotative part of the control device.

12. The device of claim 11, wherein rotation of the knob in one direction moves the followers from the position of equilibrium to the position of maximum potential, subsequent rotation of the knob in the opposite direction moves each follower from the position of maximum potential to the position of equilibrium, and further rotation in the opposite direction is mechanically prevented by a height transition in the cam blocking further rotation of each follower.

13. The device of claim 10, wherein the cam portion and follower portions have between them a position of maximum potential energy and a position of equilibrium, whereby each follower portion engages with the cam portion as the knob is rotated about the first axis to move between the maximum potential and equilibrium positions, wherein each follower is in a more compressed state near the position of maximum potential and a less compressed state near the position of equilibrium, and the cam portion includes a spring urging it toward the followers so that the knob registers to an initial position, wherein rotation of the knob in one direction moves the followers from the position of equilibrium to the position of maximum potential, and subsequent rotation of the knob in the opposite direction moves each follower from the position of maximum potential to the position of equilibrium.

14. The device of claim 13, wherein the cam is symmetrical about a median plane extending along and including the first axis.

15. The device of claim 14, wherein the median plane intersects each follower so that the two followers are opposite one another with the first axis extending therebetween.

16. The device of claim 15, wherein the cam includes radially angled cam surfaces so that increasing a spring force of the spring of the cam portion provides increased compression between the two followers and the cam, increased anti-backlash between the rotative portion and the fixed portion of the control device, and/or higher torque required for rotation of the knob in relation to the base.

17. The device of claim 13, wherein rotation of the knob is self driven toward the equilibrium position such that the knob rotates toward the equilibrium position without rotative forces being applied to the rotative part by the operator/user.

* * * * *